United States Patent
Yasui et al.

(10) Patent No.: US 9,855,162 B2
(45) Date of Patent: Jan. 2, 2018

(54) SPINAL ORTHOSIS

(71) Applicant: KAWAMURA GISHI CO., LTD., Osaka (JP)

(72) Inventors: Tadashi Yasui, Osaka (JP); Hiromitsu Nakajima, Osaka (JP); Kazuyoshi Horiuchi, Osaka (JP); Junji Katsuhira, Tochigi (JP); Takane Mitomi, Tokyo (JP)

(73) Assignee: KAWAMURA GISHI CO., LTD., Osaka (JP)

( * ) Notice: Subject to any disclaimer, the term of this patent is extended or adjusted under 35 U.S.C. 154(b) by 223 days.

(21) Appl. No.: 14/429,195

(22) PCT Filed: Oct. 1, 2012

(86) PCT No.: PCT/JP2012/075383
§ 371 (c)(1),
(2) Date: Mar. 18, 2015

(87) PCT Pub. No.: WO2014/054097
PCT Pub. Date: Apr. 10, 2014

(65) Prior Publication Data
US 2015/0223962 A1    Aug. 13, 2015

(51) Int. Cl.
*A61F 5/02* (2006.01)

(52) U.S. Cl.
CPC .......... *A61F 5/02* (2013.01); *A61F 5/024* (2013.01)

(58) Field of Classification Search
CPC ........ A61F 5/028; A61F 5/026; A61F 5/0193; A61F 5/0102; A61F 5/30;
(Continued)

(56) References Cited

U.S. PATENT DOCUMENTS 2,886,031 A * 5/1959 Robbins ............... A61F 5/024
                                                    602/19
3,220,407 A * 11/1965 Connelly ............. A61F 5/024
                                                    602/19
(Continued)

FOREIGN PATENT DOCUMENTS

JP    59-133214    9/1984
JP    4-95021      8/1992
(Continued)

OTHER PUBLICATIONS

Extended European Search Report dated Apr. 26, 2016 in European patent application No. 12885954.3.
(Continued)

*Primary Examiner* — Ophelia A Hawthorne
(74) *Attorney, Agent, or Firm* — Wenderoth, Lind & Ponack, L.L.P.

(57) ABSTRACT

A spinal orthosis includes: a pair of waist mounting members (2) fixed to both side surfaces of the waist; and a chest pressing member (3) installed to each waist mounting member. The chest pressing member includes: an arched arm (4) pivotally supported by pivots provided on both side surfaces of the waist mounting members and capable of swinging; a chest pressing body (4a) provided at an upper end portion of the arm; a pressing force giving portion (5, 6) provided at a middle part of the arm and giving a pressing force for pressing the chest pressing body to a chest.

5 Claims, 8 Drawing Sheets

(58) Field of Classification Search
CPC ...... A61F 2005/0132; A61F 2005/0172; A61F 2250/001; A61F 5/022; A61F 5/01; A61F 5/024; A61F 5/055; A61F 2005/0197; A61F 5/03; A41D 13/0512; A41D 2600/102; A41D 13/0531; A42B 3/0473; A63B 71/1291; A63B 2225/09; A63B 23/0482; A63B 71/12; A63B 2209/10; A63B 2210/50; A63B 21/4035; A63B 21/068; A63B 21/4043; A63B 22/0023; A63B 23/12; A63B 21/0622; A63B 21/4045; A63B 22/0087; A63B 23/1209; A63B 21/4031; A63B 2208/0252; A63B 21/015; A61H 1/0229; A61H 1/0244
USPC ................................... 602/19; 128/874–875
See application file for complete search history.

(56) References Cited

U.S. PATENT DOCUMENTS

| | | | |
|---|---|---|---|
| 5,176,622 A | 1/1993 | Anderson et al. | |
| 5,599,286 A | 2/1997 | Labelle et al. | |
| 6,471,665 B1* | 10/2002 | Milbourn | A61F 5/024 128/103.1 |
| 8,568,344 B2* | 10/2013 | Ferguson | A61H 3/00 602/16 |
| 2008/0161738 A1* | 7/2008 | Giesen | A61F 5/026 602/19 |
| 2010/0234783 A1* | 9/2010 | Smits | A61F 5/024 602/19 |
| 2013/0184626 A1 | 7/2013 | Kazerooni et al. | |

FOREIGN PATENT DOCUMENTS

| | | |
|---|---|---|
| JP | 9-507133 | 7/1997 |
| JP | 2011-19874 | 2/2011 |
| WO | 2012/006087 | 1/2012 |

OTHER PUBLICATIONS

International Search Report dated Nov. 13, 2012 in International Application No. PCT/JP2012/075383.
Office Action dated Jul. 12, 2016 in Japanese patent application No. 2014-539494 (with English Translation).

* cited by examiner

[Fig.1]
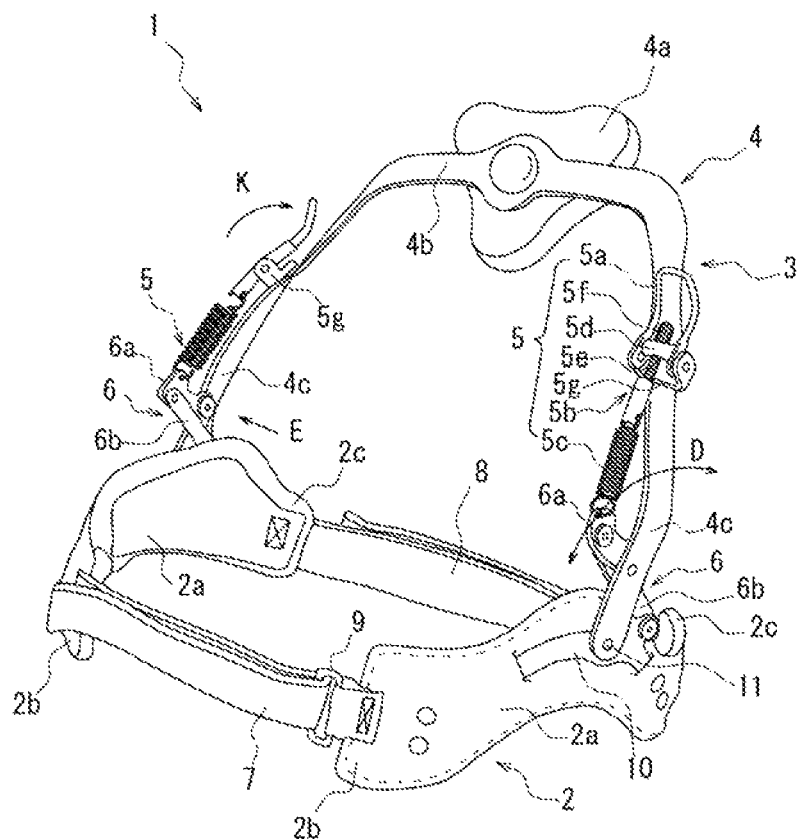

[Fig.2]
(a)
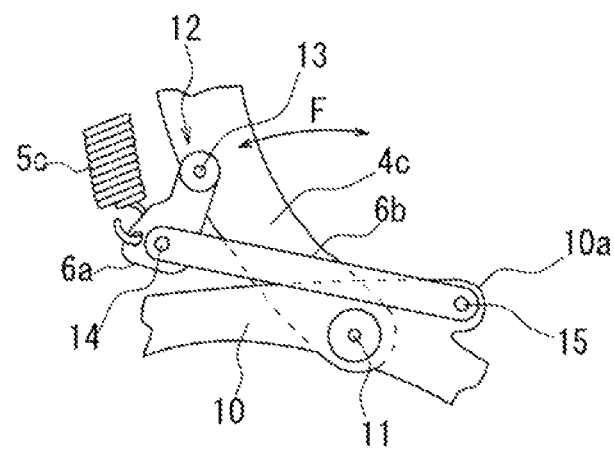
(b)
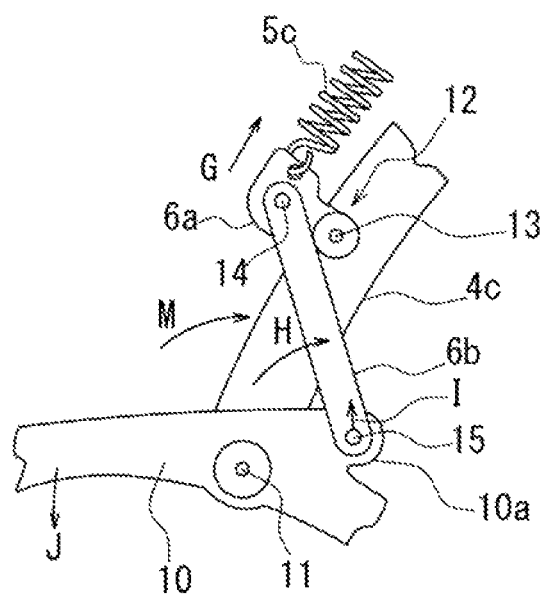

[Fig.3]
(a)
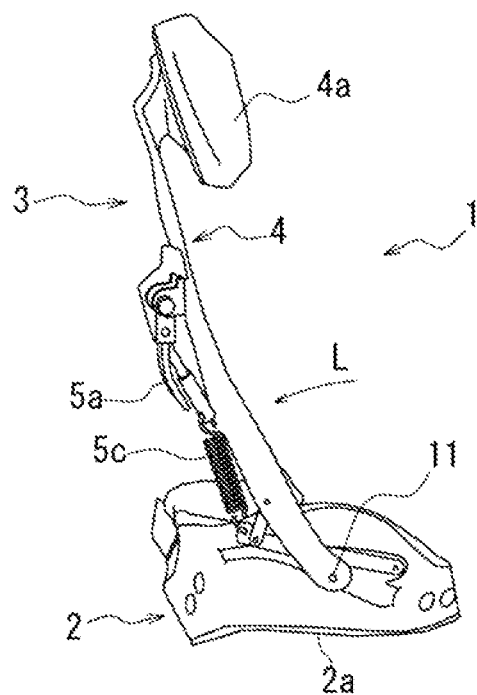
(b)
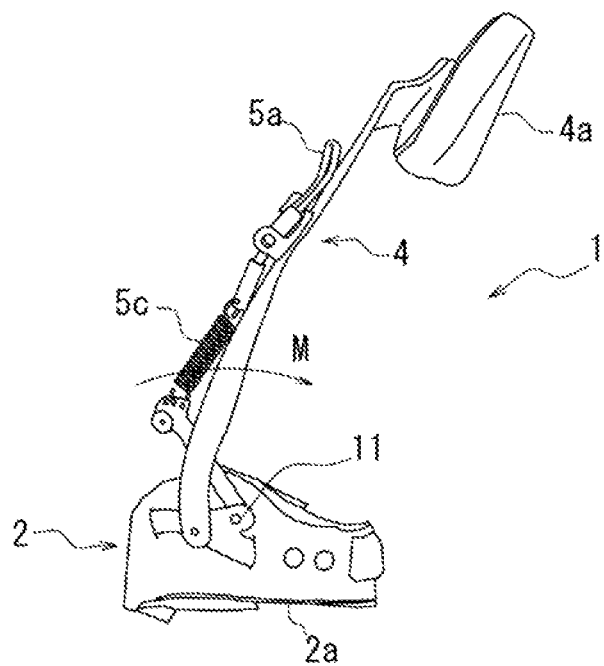

[Fig.4]
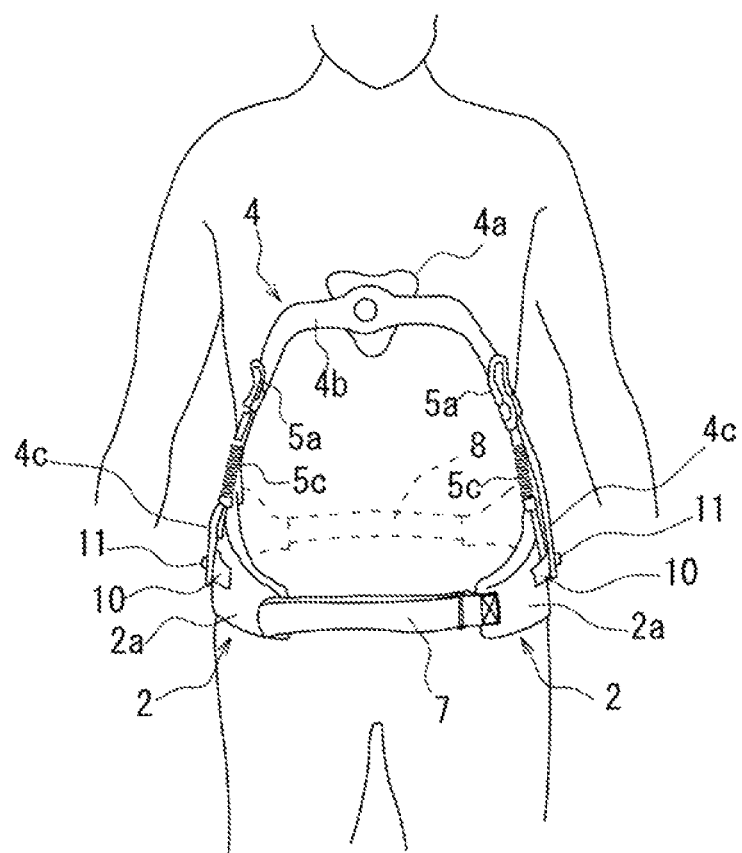

[Fig.5]
(a)
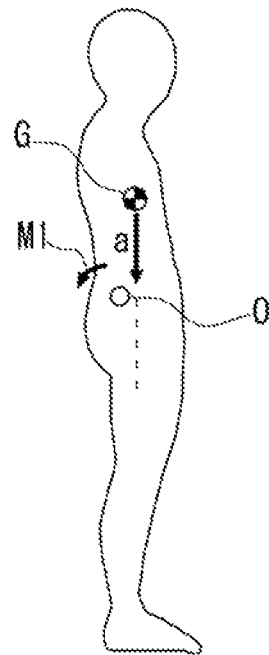
(b)
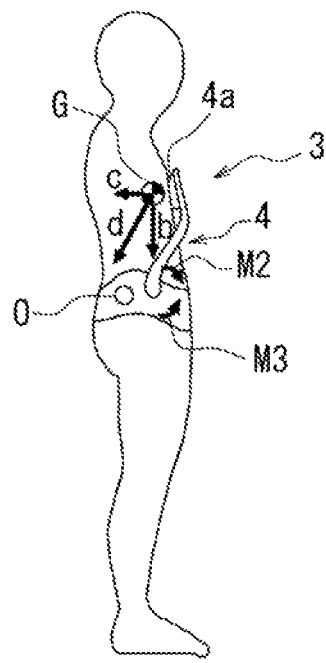

[Fig.6]
(a)
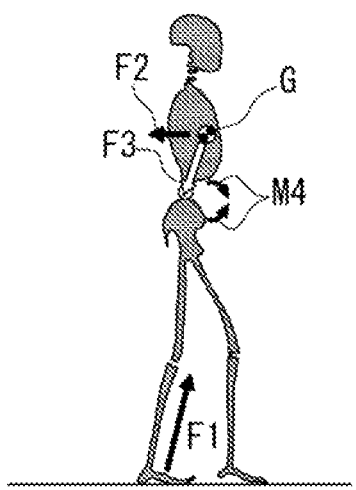
(b)
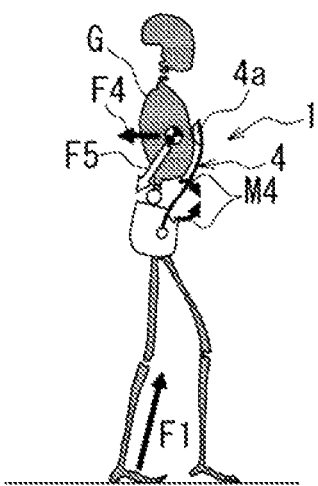

[Fig. 7]
(a)
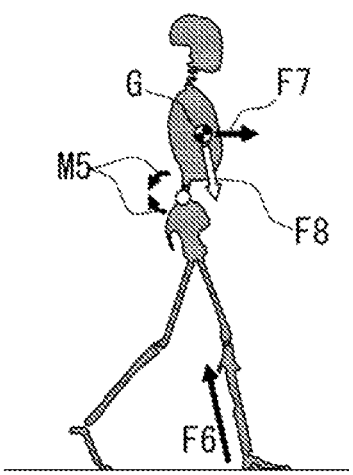
(b)
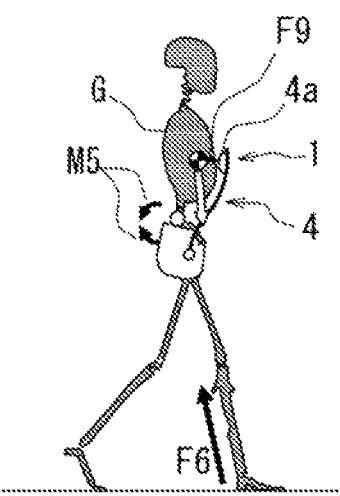

[Fig.8]
(a)
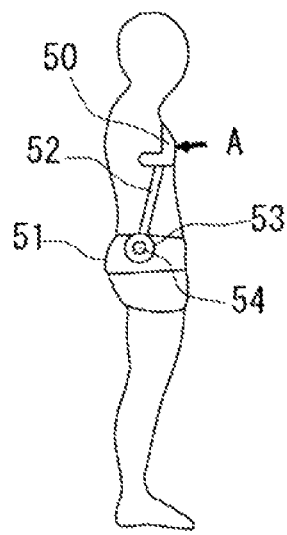
(b)
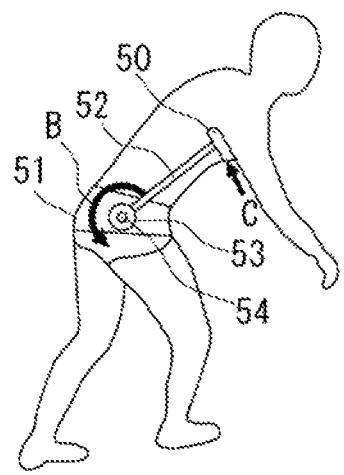

SPINAL ORTHOSIS

BACKGROUND OF THE INVENTION

1. Technical Field

The present invention relates to a spinal orthosis which can prevent back pain by reducing the burden on a waist without fixing a trunk.

2. Description of the Related Art

An extremely large number of people suffer trouble with their body due to back pain, and back pain is considered to be one of the chronic diseases.

As one means for preventing or reducing back pain, a corset having the purpose of fixing a trunk or a pelvis has been popularly used. This type of corset is mounted on a pelvis portion so as to compress the waist. With the increase of abdominal pressure, the waist becomes stable.

However, the corset has no effect in reducing the burden of load applied to the waist. As the corset fixes the trunk, the corset has a disadvantage in that a movable range of the waist is constricted thus weakening abdominal muscles.

In view of the above, the applicant of the present application has developed a spinal orthosis which can reduce the burden of load on a waist, and at the same time, does not weaken the function of abdominal muscles. The applicant has previously filed a patent application on the spinal orthosis (see Japanese Patent Publication No. 2011-19874A, for example).

As shown in FIG. 8, such a spinal orthosis includes: an upper support body 50 which is brought into contact with a trunk; and a waist support body 51 fixed to a waist. The upper support body 50 is connected to both left and right side portions of the waist support body 51 by way of a pair of left and right support struts 52 (only the support strut 52 on a viewer's side is shown in the drawing), and a joint device 53 is mounted on each connecting portion.

The joint device 53 includes: a rotary shaft 54 for rotating the support strut 52 about a horizontal axis; and a biasing mechanism which acts so as to bias the upper support body 50 in a direction indicated by an arrow A by a spring thus pulling up an upper body of a user which is in contact with the upper support body 50.

According to the spinal orthosis having the above-mentioned constitution, as shown in FIG. 8(a), a resistance force is not generated in the spring when the support strut 52 is not rotated about the rotary shaft 54. On the other hand, when a trunk is bent frontwardly as shown in FIG. 8(b), the support strut 52 is rotated in the rightward direction about the rotary shaft 54 so that a resistance force is accumulated in the spring, a rotational moment in a direction indicated by an arrow B is generated in the support strut 52 by such a resistance force, and the upper support body 50 presses a chest of the upper body in a direction indicated by an arrow C. As a result, a load applied to the waist can be reduced.

SUMMARY OF THE INVENTION

1. Problems to be Solved by the Invention

However, the above-mentioned conventional spinal orthosis adopts the constitution where the trunk is fixed by the waist support body 51 by enveloping the periphery of the waist. Accordingly, when a sitting posture or walking continues for a long time or the sitting or walking is repeatedly performed, there is a possibility that the mounting position of the spinal orthosis becomes displaced. Further, the joint portion which includes the biasing mechanism projects from a side surface of the waist support body 51 and hence, there exists a problem that a user's hand comes into contact with the joint portion when the user swings his hands in the longitudinal direction while walking. Accordingly, there is room for improving this spinal orthosis in realizing the practical use of the spinal orthosis.

The present invention has been made by taking into account the above-mentioned problems of the conventional spinal orthosis, and it is an object of the present invention to provide a spinal orthosis which can be mounted for a long time without restricting various operations of a body of a user, thus preventing back pain by reducing the load applied to a waist of the user.

2. Means for Solving the Problems

The spinal orthosis of the invention comprises: a pair of waist mounting members fixed to both side surfaces of the waist; and a chest pressing member installed to the each waist mounting member. The chest pressing member includes: an arched arm pivotally supported by pivots provided on both side surfaces of the waist mounting members and capable of swinging; a chest pressing body provided at an upper end portion of the arm; and a pressing force giving portion provided at a middle part of the arm and giving a pressing force for pressing the chest pressing body to a chest.

In this invention, the middle part of the arm corresponds to between a spina iliaca anterior superior and a lower sternum under a mounting state of the orthosis.

In this invention, the pressing force giving portion may comprise a spring portion and a link mechanism converting an energizing force in a linear direction generated by the spring portion into a force in the arm rotation direction.

In this invention, it is desirable to comprise an operating lever by which the spring portion is switched to a compressed state or an uncompressed state.

In this invention, it is preferable that the link mechanism slightly rotates the waist mounting member with a front-down on the pivot under the compressed state of the spring portion.

In this invention, it is preferable that the waist mounting member has a pair of fixing pads to grip a pelvis from both sides of the pelvis.

In this invention, the waist mounting member can be fixed to the waist by fastening a belt provided at an abdomen side and at a back side.

3. Effect of the Invention

According to the spinal orthosis of the present invention, the spinal orthosis can be mounted for a long time without restricting various operation of a body of a user thus preventing back pain by reducing a load applied to a waist of the user.

BRIEF DESCRIPTION OF THE DRAWINGS

FIG. 1 is a perspective view showing the overall constitution of a spinal orthosis according to the present invention.

FIG. 2(a) and FIG. 2(b) are enlarged side views for describing an operation of a link mechanism.

FIG. 3(a) is a side view of a chest pressing member in a non-pressing posture, and FIG. 3(b) is a side view of the chest pressing member in a pressing posture.

FIG. 4 is a front view showing a mounting state of the spinal orthosis according to the present invention.

FIG. 5(a) and FIG. 5(b) are explanatory views for describing an advantageous effect of the spinal orthosis of the present invention.

FIG. 6(a) and FIG. 6(b) are explanatory views for describing an advantageous effect of the spinal orthosis of the present invention when walking.

FIG. 7(a) and FIG. 7(b) are explanatory views for describing an advantageous effect of the spinal orthosis of the present invention when walking.

FIG. 8(a) and FIG. 8(b) are explanatory views for describing an operation of a conventional spinal orthosis.

DETAILED DESCRIPTION OF THE INVENTION

Hereinafter, the present invention is described in detail based on an embodiment shown in the drawings.

1. Constitution of Spinal Orthosis

In FIG. 1, a spinal orthosis 1 of the present invention is mainly constituted of: a pair of left and right waist mounting members 2 fixed to a waist; and a chest pressing member 3 installed to the waist mounting member 2. The chest pressing member 3 further includes: an arched arm 4 pivotally supported by pivots provided on both side surfaces of the waist mounting member 2 and capable of swinging in the longitudinal direction; a chest pressing pad (chest pressing body) 4a provided at an upper end portion of the arm; and a spring portion 5 and a link mechanism 6 provided at a middle portion of the arm 4 and giving a pressing force for pressing the chest pressing pad 4a to a chest. The spring portion 5 and the link mechanism 6 function as a pressing force giving portion.

The constitutions of the respective portions are described in detail hereinafter.

1-1 Waist Mounting Member

The waist mounting member 2 has a pair of fixing pads 2a to grip a pelvis from both sides of the pelvis. These fixing pads 2a respectively include a synthetic resin molding plate formed in conformity with a shape of a side portion of the pelvis and having a thickness of 2 mm to 3 mm as a core member (not shown in the drawing). A cushion member is adhered to an inner surface (waist close contact side) of the core member, and the cushion member is covered with a cloth material having air permeability. An outer surface (waist non-close contact side) of the core member is covered with synthetic leather.

As a synthetic resin for forming the core member, for example, a polyethylene resin, a soft polyethylene resin, a polypropylene resin or the like can be used.

Front-side end portions 2b of the pair of fixing pads 2a can be connected to each other by fastening a front belt 7, and such connection of the front-side end portions 2b can be released by loosening the front belt 7. Also, rear-side end portions 2c of the pair of fixing pads 2a can be connected to each other by fastening a rear belt 8, and such connection of the rear-side end portions 2c can be released by loosening the rear belt 8.

In the drawing, symbol 9 indicates a buckle. The front belt 7 passes through the buckle 9 and is folded. Folded and overlapping portions of the front belt 7 can be fixed to each other by a Velcro fastener. The rear belt 8 has the substantially same constitution as the front belt 7.

1-2 Chest Pressing Member 1-2-1 Arm

The arm 4 which is a constitutional part of the chest pressing member 3 is made of a metal strip installed on the above-mentioned pair of fixing pads 2a in an arched shape, wherein a lateral plate portion 4b which forms an upper portion of the arm has a plate surface thereof disposed parallel to a chest of a user, and the chest pressing pad (chest pressing body) 4a having an approximately inverted triangular shape for pressing the chest is provided at the center of the arm. The chest pressing pad 4a is formed by covering a core member having resiliency and made of soft polyethylene with a cushion member.

Left and right longitudinal plate portions 4c, 4c of the arm 4 are formed in a downwardly spreading manner, and are twisted with respect to the above-mentioned lateral plate portion 4b by approximately 90 degrees and hence, plate surfaces of the left and right longitudinal plate portions 4c, 4c are disposed parallel to side surfaces of the waist.

Due to such a constitution, when the spinal orthosis 1 is mounted on the body of a patient suffering from back pain, as shown in FIG. 4, the longitudinal plate portions 4c of the arm 4 do not pass along side surfaces of an upper part of the body of the patient, and are raised obliquely from the waist mounting member 2 along a chest of the patient. Accordingly, the swing of the arm of the patient does not interfere with the arm 4 when walking.

A lower end (arm proximal end portion) of the longitudinal plate portion 4c is connected to a base metal fitting 10 fixed to the core member of the waist mounting member 2 by way of a pivot shaft 11. Due to such a constitution, the arm 4 is swingable in a direction indicated by an arrow D about the pivot shaft 11.

1-2-2 Link Mechanism

FIG. 2 is side view of the link mechanism 6 shown in FIG. 1 as viewed from a direction indicated by an arrow E. FIG. 2(a) shows a posture of the link mechanism 6 in a state where the chest is not pressed, and FIG. 2(b) shows the posture of the link mechanism 6 in a state where the chest is pressed.

In FIG. 2(a), a first link connecting portion 10a is formed on the base metal fitting 10 such that the first link connecting portion 10a is raised from the base metal fitting 10. On the other hand, a second link connecting portion 12 is mounted on a lower portion of the longitudinal plate portion 4c, and one end of a swing member 6a is connected to the second link connecting portion 12 by way of a pin 13. The other end of the swing member 6a is connected to one end of a link 6b by way a pin 14, and the other end of the link 6b is connected to the first link connecting portion 10a by way of a pin 15.

In a state where the spring portion 5 does not give a chest pressing force to the arm 4, the longitudinal plate portion 4c is freely swingable in a direction indicated by an arrow F, and the link 6b is moved in a leftward direction to a position where the link 6b comes into contact with the base metal fitting 10 and is folded at the position.

In FIG. 2(b), when an operating lever 5a described later is operated so that the spring portion 5 gives an energizing force to the arm 4, the swing member 6a is pulled up in a direction indicated by an arrow G about the pin 13. Accordingly, the link 6b is rotated in a direction indicated by an arrow H about the pin 15 and the arm 4 is rotated in a direction indicated by an arrow M.

When the link 6b is rotated in a direction indicated by an arrow H, a force in an upward direction (direction indicated by an arrow I) acts on the first link connecting portion 10a and hence, a force in a downward direction (direction indicated by an arrow J) acts on a distal end side of the base metal fitting 10. That is, an operation which slightly rotates the waist mounting member 2 frontwardly and downwardly is performed.

1-2-3 Spring Portion

As shown in FIG. 1, the spring portion 5 includes: the operating lever 5a; a pressing force adjusting part 5b connected to the operating lever 5a; a tensile coil spring 5c which extends between the pressing force adjusting part 5b and the swing member 6a. The spring portions 5 are respectively arranged on middle parts of the left and right longitudinal plate portions 4c, 4c of the arm 4. To be more specific, the spring portions 5 are respectively arranged at portions between spina iliaca anterior superior and a lower sternum under a mounting state of the spinal orthosis 1.

The pressing force adjusting part 5b includes a threaded portion 5e which penetrates a rod 5d to which the operating lever 5a is connected. A chest pressing force can be increased by threadedly fastening an adjustment nut 5f with the threaded portion 5e, while the chest pressing force can be decreased by releasing the adjustment nut 5f. In the drawings, 5g indicates a fitting by which the operating lever 5a is mounted on the arm 4.

The operating lever 5a is provided for switching the tensile coil spring 5c which constitutes the spring portion 5 between a compressed state and an uncompressed state. When the operating lever 5a is lifted (in a direction indicated by an arrow K) to a position where the operating lever 5a is brought into contact with the arm 4, the tensile coil spring 5c is extended so that an energizing force is generated in the tensile coil spring 5c. An energizing force in a straight line direction generated by the tensile coil spring 5c is converted into a force in an arm rotating direction by the link mechanism 6 and such a force becomes a chest pressing force which pushes the chest pressing pad 4a to a chest of a patient suffering from back pain.

2. Manner of Operation of Spinal Orthosis

FIG. 3(a) is a side view showing a state where an energizing force is not generated in the spring portion 5, and FIG. 3(b) is a side view showing a state where an energizing force is generated in the spring portion 5. Provided that both drawings show the operation of the spinal orthosis 1 in a state where the spinal orthosis 1 is not mounted on a patient suffering from back pain.

FIG. 3(a) corresponds to the operation of the link mechanism 6 shown in FIG. 2(a). Since the operating lever 5a is made to fall downward, an energizing force is not generated in the tensile coil spring 5c and hence, the arm 4 can be made to fall toward a left side (direction indicated by an arrow L) and a patient suffering from back pain can smoothly mount the spinal orthosis 1 on his body in this state.

FIG. 3(b) corresponds to the operation of the link mechanism 6 shown in FIG. 2(b). By lifting the operating lever 5a upward, an energizing force is generated in the tensile coil spring 5c, and a chest pressing force is generated by way of the link mechanism 6 and hence, the arm 4 is rotated in a direction indicated by an arrow M about a pivot shaft 11.

3. Working of Spinal Orthosis

FIG. 5 is side view for describing an advantageous effect acquired by the spinal orthosis 1, wherein FIG. 5(a) shows a state where the spinal orthosis 1 is not mounted on a user, and FIG. 5(b) shows a state where the spinal orthosis 1 is mounted on the user.

In FIG. 5(a), in a normal standing posture, the center of gravity G of an upper trunk which is obtained by combining the center of gravity of a head, the center of gravity of both arms and the center of gravity of the trunk above a pelvis is positioned in front of a waist joint center position O.

Accordingly, a vector "a" of gravity applied to the center of gravity G of the upper trunk passes a front side of the waist portion joint center position O and hence, a moment M1 which bends the trunk backward is generated in the waist due to an action of erector muscles of spine and the like.

On the other hand, when the spinal orthosis 1 of the present invention is mounted on a user, as shown in FIG. 5(b), due to a chest pressing force generated by the pressing pad 4a of the chest pressing member 3, the center of gravity G of the upper trunk constantly receives a force which pushes back the upper trunk rearward.

Accordingly, a resultant force "d" of a vector "b" of gravity applied to the center of gravity G of the upper trunk and a vector "c" of the above-mentioned pressing force passes behind the waist joint center position O. Accordingly, a moment M2 which bends the trunk frontward can be generated by working of abdominal muscles at a waist joint.

When a chest pressing force is applied to an upper part of the body of the user by the chest pressing member 3, a force which pushes the pelvis frontward from a rear side is generated as a reaction.

Accordingly, the trunk is pressed rearward about a joint point of the waist and the pelvis receives a force which presses the pelvis in a frontward direction and hence, the body of the user intends to take a balance by generating a moment by itself using a trunk muscle group. By making the trunk muscle group work in this manner, back pain can be prevented.

Further, when the trunk is bent frontward, the arm 4 is rotated in the rightward direction about the pivot shaft 11. Accordingly, the tensile coil spring 5c of the spring portion 5 is further stretched so that an energizing force is increased. A rotational moment M3 is generated by the increased energizing force thus generating a resistance force in the direction that the upper part of the body of the user which is bent frontward is raised. As a result, a load applied to the waist can be reduced.

4. Working of Spinal Orthosis when Walking

FIG. 6(a) shows a state where the spinal orthosis 1 is not mounted on a user and one of his legs is in contact with the ground, and FIG. 6(b) shows a state where the spinal orthosis 1 is mounted on the user and one of his legs is in contact with the ground.

In FIG. 6(a), when the user receives a floor reaction force F1 directed in a frontward direction by kicking his leg on a rear side frontwardly, a rearward inertial force F2 is applied to the trunk and hence, an abdominal muscle moment M4 becomes necessary. Symbol F3 indicates a resultant force of the inertial force F2 and the gravity applied to the center of gravity G.

In FIG. 6(b), when the spinal orthosis 1 is mounted on the user, an inertia-pressing force F4 which is obtained by adding a chest pressing force generated by the spinal orthosis 1 to an inertial force applied rearward to the trunk of the user is applied. Accordingly, compared to the case where the spinal orthosis 1 is not mounted on the user, the action of the abdominal muscle moment M4 is enhanced. Symbol F5 indicates a resultant force of the inertia-pressing force F4 and the gravity applied to the center of gravity G.

FIG. 7(a) shows a state where the spinal orthosis 1 is not mounted on a user and both of his legs are in contact with the ground, and FIG. 7(b) shows a state where the spinal orthosis 1 is mounted on the user and both of his legs are in contact with the ground.

In FIG. 7(a), in a state where both legs of the user are in contact with the ground, the user receives a rearward floor reaction force F6 when the leg on a front side of the body is braked, and a frontward inertial force F7 is applied to the trunk and hence, a spinal muscle moment M5 becomes necessary. Symbol F8 indicates a resultant force of the inertial force F7 and the gravity applied to the center of gravity G.

In FIG. 7(b), when the spinal orthosis 1 is mounted on the user, a chest pressing force generated by the spinal orthosis 1 acts against the frontward inertial force F7 in the reverse direction and hence, a frontward inertial force F9 smaller than the frontward inertial force F7 is generated.

Accordingly, compared with the case where the spinal orthosis is not mounted on the user, the spinal muscle moment M5 becomes small and, eventually, a load applied to erector muscles of spine can be reduced.

That is, when the user walks while the spinal orthosis 1 of the present invention is mounted on his body, the load applied to the erector muscles of spine can be lowered while increasing activity of abdominal rectus muscles and hence, a load applied to the waist of the user when walking can be reduced.

The arm adopted in the above-mentioned embodiment is constituted of an integral arm which is pivotally supported on pivot shafts mounted on both side surfaces of the waist mounting members and is swingable. However, the arm which can be adopted in the present invention is not limited to such an arm, and arms (divided arms) may be extended independently from both side surfaces of the waist mounting members.

The divided arms may have upper portions connected to each other, and a chest pressing pad may be mounted on the connecting portion. Alternatively, the upper portions of the divided arms may not be connected to each other, and a chest pressing pad may be mounted on the upper portions of the respective arms.

When the divided arms are adopted, an energizing force generated by the spring portion 5 may be adjusted such that the energizing force differs between left and right sides.

In the above-mentioned embodiment, the shape of the arm is formed in left and right symmetry. However, the shape of the arm may be formed in left and right asymmetry or in opposite directions with respect to the front and rear directions corresponding to physique, a symptom or the like of a patient suffering from back pain.

The present invention can reduce a load applied to a waist and prevent back pain without fixing a trunk and hence, the present invention is applicable to the treatment of a patient suffering from back pain or the prevention of back pain of a person engaged in care or load carrying operation.

DESCRIPTION OF REFERENCE SIGNS

1 Spinal orthosis
2 Waist mounting member
2a Fixing pad
3 Chest pressing member
4 Arm
4a Chest pressing pad
4b Lateral plate portion
4c Longitudinal plate portion
5 Spring portion
5a Operating lever
5b Pressing force adjusting part
5c Tensile coil spring
5d Rod
5e Threaded portion
5f Adjustment nut
6 Link mechanism
6a Swing member
6b Link
7 Front belt
8 Rear belt
9 Buckle
10 Base metal fitting
10a First link connecting portion
11 Pivot
12 Second link connecting portion
13~15 Pin

The invention claimed is:

1. A spinal orthosis comprising:
a pair of waist mounting members adapted to be fixed to opposite sides of a user's waist; and
a chest pressing member mounted on each of the waist mounting members,
wherein the chest pressing member includes:
an arched arm pivotally supported by pivots provided on both side surfaces of the waist mounting members and being capable of swinging;
a chest pressing body provided at an upper end portion of the arm; and
a pressing force giving portion provided at a middle part of the arm and being configured to apply a pressing force for pressing the chest pressing body to a chest of the user,
wherein the pressing force giving portion comprises:
a spring portion; and
a link mechanism for converting an energizing force in a linear direction generated by the spring portion into a force in the arm rotation direction,
the spinal orthosis further comprising an operating lever by which the spring portion is switched to a compressed state or an uncompressed state.

2. The spinal orthosis according to claim 1, wherein the link mechanism slightly rotates the waist mounting member with a front-down on the pivot under the compressed state of the spring portion.

3. The spinal orthosis according to claim 1, wherein the pair of waist mounting members have a pair of fixing pads to grip a pelvis from both sides of the pelvis.

4. The spinal orthosis according to claim 1, further comprising a front belt provided at front sides of the waist mounting members and a rear belt provide at rear sides of the waist mounting members,
wherein the waist mounting members can be fixed to the user's waist by fastening the front and rear belts.

5. The spinal orthosis according to claim 1, wherein the middle part of the arm is configured to corresponds to between a spina iliaca anterior superior and a lower sternum under a mounting state of the orthosis.

* * * * *